US012167942B2

(12) United States Patent
Tadano et al.

(10) Patent No.: US 12,167,942 B2
(45) Date of Patent: Dec. 17, 2024

(54) SURGERY ASSISTING DEVICE (71) Applicant: RIVERFIELD INC., Tokyo (JP)

(72) Inventors: Kotaro Tadano, Tokyo (JP); Masataka Suzuki, Tokyo (JP)

(73) Assignee: RIVERFIELD INC., Tokyo (JP)

( * ) Notice: Subject to any disclaimer, the term of this patent is extended or adjusted under 35 U.S.C. 154(b) by 692 days.

(21) Appl. No.: 17/425,878

(22) PCT Filed: Dec. 19, 2019

(86) PCT No.: PCT/JP2019/049857
§ 371 (c)(1),
(2) Date: Jul. 26, 2021

(87) PCT Pub. No.: WO2020/158232
PCT Pub. Date: Aug. 6, 2020

(65) Prior Publication Data
US 2022/0160458 A1  May 26, 2022

(30) Foreign Application Priority Data

Jan. 29, 2019  (JP) .................................. 2019-013248

(51) Int. Cl.
*A61B 34/37* (2016.01)
*A61B 34/30* (2016.01)
*A61B 90/50* (2016.01)

(52) U.S. Cl.
CPC .............. *A61B 90/50* (2016.02); *A61B 34/37* (2016.02); *A61B 2034/301* (2016.02); *A61B 2034/302* (2016.02); *A61B 2090/506* (2016.02)

(58) Field of Classification Search
CPC ... A61B 90/50; A61B 34/37; A61B 2034/301; A61B 2034/302; A61B 2090/506; A61B 34/30; B25J 9/1065
See application file for complete search history.

(56) References Cited

U.S. PATENT DOCUMENTS 6,786,896 B1* 9/2004 Madhani ................ A61B 34/30
606/1
2004/0261179 A1* 12/2004 Blumenkranz ........ B25J 9/0018
5/630
(Continued)

FOREIGN PATENT DOCUMENTS

EP        3388015 A1    10/2018
JP    2010-507792 A     3/2010
(Continued)

OTHER PUBLICATIONS

Notice of Reasons for Refusal dated Mar. 15, 2022 from the Japanese Patent Office in JP Application No. 2019-13248.
(Continued)

*Primary Examiner* — Masud Ahmed
*Assistant Examiner* — Dylan M Katz
(74) *Attorney, Agent, or Firm* — Sughrue Mion, PLLC (57) ABSTRACT A surgery assisting device holds a surgical instrument having an end to be inserted into a body cavity of a patient, and controls one or more of a position or an orientation of the surgical instrument. The surgery assisting device includes a first arm and second arms. The first arm has a first end supported by a base and includes a first movable part having movement with one or more degrees of freedom. The second arms are arranged at a second end of the first arm and hold the surgical instrument. Each of the second arms includes second movable parts having movement with five or more degrees of freedom.

21 Claims, 8 Drawing Sheets

(56) References Cited

U.S. PATENT DOCUMENTS

| | | | |
|---|---|---|---|
| 2006/0167440 A1* | 7/2006 | Cooper | A61B 34/71 606/1 |
| 2010/0094312 A1 | 4/2010 | Ruiz Morales et al. | |
| 2013/0012930 A1 | 1/2013 | Ruiz Morales et al. | |
| 2018/0098817 A1 | 4/2018 | Nichogi | |
| 2018/0283019 A1* | 10/2018 | Telleria | B24B 55/06 |
| 2018/0360553 A1* | 12/2018 | Nakanishi | A61B 34/37 |
| 2019/0231460 A1 | 8/2019 | DiMalo | |
| 2021/0059783 A1 | 3/2021 | Haraguchi et al. | |

FOREIGN PATENT DOCUMENTS

| | | |
|---|---|---|
| JP | 2012-020156 A | 2/2012 |
| WO | 2011/143020 A1 | 11/2011 |
| WO | 2015/142943 A1 | 9/2015 |
| WO | 2016/203858 A1 | 12/2016 |
| WO | 2018/052796 A1 | 3/2018 |

OTHER PUBLICATIONS

International Search Report for PCT/JP2019/049857 dated Feb. 2, 2020 [PCT/ISA/210].
Written Opinion for PCT/JP2019/049857 dated Feb. 2, 2020 [PCT/ISA/237].
Notice of Reasons for Refusal for JP 2019-013248 dated Jan. 12, 2021.
Decision of Refusal for JP 2019-013248 dated May 18, 2021.
Extended European Search Report dated Oct. 10, 2022 Issued in European Application No. 19913705.0.
Reconsideration Report by Examiner before Appeal dated Aug. 5, 2021 from the Japanese Patent Office in JP Application No. 2019-013248.
International Preliminary Report on Patentability with the translation of Written Opinion dated Aug. 12, 2021 from the International Bureau in International Application No. PCT/JP2019/049857.

* cited by examiner

SURGERY ASSISTING DEVICE

CROSS-REFERENCE TO RELATED APPLICATION

This international application is a National Stage of International Application No. PCT/JP2019/049857 filed Dec. 19, 2019, which is based on and claims priority to Japanese Patent Application No. 2019-013248 filed on Jan. 29, 2019 with the Japan Patent Office, the entire contents of each of which being herein incorporated by reference in their entireties.

TECHNICAL FIELD

The present disclosure relates to a surgery assisting device.

BACKGROUND ART

In recent years, various surgery assisting robots, such as robots that assist endoscopic surgery, have been proposed (see, for example, Patent Document 1). In many cases, the surgery assisting robots each comprise a robot arm (hereinafter also referred to as "arm") that holds an instrument used in surgery, such as an endoscope or forceps, and that operates the surgical instrument.

In the case of endoscopic surgery, setting, which is insertion of the surgical instrument into a body cavity, is performed. The surgical instrument is inserted into the body cavity from a port aperture provided at a body surface of a patient via a trocar, or directly not via a trocar.

An operator of endoscopic surgery performs a procedure by manipulating the surgery assisting robot. In accordance with the operator's manipulation, the surgery assisting robot operates the surgical instrument it holds, with a pivot point as the center. The pivot point is set at a specified spot (e.g., on a shaft axis of the surgical instrument) with respect to the held surgical instrument. A configuration in which the pivot point is set structurally is in widespread use. To the patient with the surgical instrument inserted, the pivot point is set within the port aperture and at an intermediate position between an outer surface and an inner surface of an abdominal wall, a chest wall, or other wall.

The surgical instrument, when its orientation and/or arrangement position is changed by manipulation, passes through the pivot point set as described above. At this time, the surgical instrument changes its orientation and/or arrangement position with the pivot point set within the port aperture as the center. This results in preventing tissue near the body surface of the patient from being subjected to an increased load.

PRIOR ART DOCUMENTS

Patent Documents

Patent Document 1: Japanese Unexamined Patent Application Publication No. 2012-020156

SUMMARY OF THE INVENTION

Problems to be Solved by the Invention

For example, when the position of the pivot point deviates from the shaft axis of the surgical instrument, the surgical instrument changed in its orientation and/or arrangement position presses an inner peripheral surface of the port aperture. As a result, the tissue near the body surface of the patient is subjected to an increased load, and the tissue may be damaged.

Therefore, in the setting for endoscopic surgery, it is important to arrange the arm of the surgery assisting robot and the surgical instrument at appropriate positions. Patent Document 1 discloses a technique for arranging the arm and the surgical instrument at appropriate positions by means of a configuration comprising an orienting platform, a set-up arm connected to the orienting platform, and a manipulator supported by the set-up arm.

Specifically, the orienting platform is arranged so as to be movable relative to a platform linkage, thus moving the orienting platform. This provides a rough alignment of the set-up arm, the manipulator, and the surgical instrument held by the manipulator.

After that, a relative positioning of the set-up arm with respect to the orienting platform is performed, and orientation alignment of the manipulator is performed. Performed between the positioning of the set-up arm and the orientation alignment of the manipulator is insertion of the surgical instrument through the trocar.

However, the configuration described in Patent Document 1 has a number of processes of positioning and orientation alignment performed in the setting, thus having caused a problem of making the setting troublesome. In addition, since the pivot point with respect to the surgical instrument is fixed mechanically, the position of the pivot point with respect to the patient has to be adjusted accurately, thus also having caused a problem of readily impairing convenience of the setting.

It is desirable that the present disclosure provide a surgery assisting device allowing for facilitation of setting.

Means for Solving the Problems

A surgery assisting device of the present disclosure is a surgery assisting device configured to hold a surgical instrument having an end to be inserted into a body cavity of a patient, and configured to control at least one of a position or an orientation of the surgical instrument, and comprises: a first arm having a first end supported by a base and comprises a first movable part having movement with at least one degree of freedom; and second arms arranged at a second end of the first arm and configured to each hold the surgical instrument, the second arms each comprising second movable parts having movement with at least five degrees of freedom in total.

Such a configuration makes it possible to perform setting by manipulating only the second arm due to provision of the second arm arranged to the first arm with the second movable parts, which achieve at least five degrees of freedom. For example, as compared with a case in which setting is performed by manipulating both set-up arms and manipulators like a technique described in Patent Document 1, the number of the manipulators to be manipulated is less, thus enabling easier setting.

The first movable part and the second movable parts may be configured to operate in accordance with an external force applied from the outside of the surgery assisting device, or may be configured to operate with a motive power transmitted from a motive power generator, such as an actuator or an electric motor, provided in the surgery assisting device.

Further, it is preferred that all of the second movable parts be configured to be operable in a state where the surgical instrument is inserted in the body cavity. In other words, it is preferred that none of the second movable parts be fixed in movement, in the state where the surgical instrument is inserted in the body cavity. "Fixed in movement" refers to a state where movement is unnecessary or not permitted during performance of surgery procedures.

Due to the configuration in which all of the second movable parts are operable in the state where the surgical instrument is inserted in the body cavity, a movable range of the surgical instrument is ensured more easily than in the technique described in Patent Document 1. For example, the surgical instrument inserted in a port aperture provided at a body surface of the patient can be easily moved into another port aperture. In addition, even when a relative position of the port aperture with respect to the surgery assisting device is changed for the reason such as increase/decrease in gas within the body cavity of the patient, the surgical instrument is allowed to follow such change easily.

In the above-described disclosure, it is preferred that a second end of each of the second arms be provided with a holder to hold the surgical instrument, the second end being on a side opposite to a first end supported by the first arm.

According to such a configuration, since the surgical instrument can be held at the second end, which is a distal end of the second arm, a movable range of the surgical instrument is ensured more easily than in the technique described in Patent Document 1.

In the above-described disclosure, it is preferred that the surgical instrument comprise a shaft with a long shaft shape having an end to be inserted into the body cavity, and an operating part arranged at the end of the shaft and used for surgery operation.

According to such a configuration, the surgical instrument comprises the shaft and the operating part. This makes it easier to insert the shaft into the port aperture provided at the body surface of the patient and to arrange the operating part within the body cavity of the patient.

In the above-described disclosure, it is preferred that a controller to control movements of the second movable parts be further provided and that the controller be configured to control the movements of the second movable parts so that a pivot point set in advance is positioned on the shaft when changing at least one of the orientation or an arrangement position of the surgical instrument.

According to such a configuration, since the movements of the second movable parts are controlled so that the pivot point is positioned on the shaft, even when the orientation and/or the arrangement position of the surgical instrument are/is changed, the shaft can pass through the pivot point. In other words, pivoting movement is enabled.

In the above-described disclosure, it is preferred that sensors to detect displacements in the second movable parts be provided and that the controller be configured to perform an arithmetic processing for estimating a position of the pivot point based on information on the displacements detected by the sensors.

According to such a configuration, since the position of the pivot point is estimated based on the information on the displacements in the second movable parts, the pivoting movement in the second arm is facilitated. Further, control of the movements of the second movable parts by the controller is enabled based on all of the information on the displacements in the second movable parts. In other words, no case occurs in which control of some of the second movable parts and control of the others are performed by different controllers. That is, the controller is configured such that the movements of the second movable parts are controlled by a single control system based on all of the information on the displacements in the second movable parts.

In the above-described disclosure, it is preferred that the second movable parts have three degrees of freedom, which are movements in three directions intersecting with one another in the surgical instrument, and two degrees of freedom, which are rotations about two axes intersecting with a central axis of the shaft and also intersecting with each other.

According to such a configuration, since the second movable parts have three degrees of freedom, which are movements in three directions intersecting with one another in the surgical instrument, and two degrees of freedom, which are rotations about two axes intersecting with a central axis of the shaft and also intersecting with each other, setting can be performed by manipulating only the second arm.

Effects of the Invention

The surgery assisting device of the present disclosure produces an effect of facilitating setting of the surgery assisting device by providing the second movable parts, which achieve at least five degrees of freedom, to the second arm arranged to the first arm.

EXPLANATION OF REFERENCE NUMERALS

1 . . . surgery assisting robot (surgery assisting device), 20 . . . first arm, 23 . . . joint (first movable part), 24 . . . fitting part (first movable part), 30 . . . second arm, 31 . . . rotating part (second movable part), 31$s$ . . . rotation sensor (sensor), 35$p$ . . . pin (second movable part), 35$s$ . . . first link sensor (sensor), 36$p$ . . . pin (second movable part), 36$s$ . . . second link sensor (sensor), 42 . . . first joint (second movable part), 42$s$ . . . first joint sensor (sensor), 43 . . . second joint (second movable part), 43$s$ . . . second joint sensor (sensor), 44 . . . third joint (second movable part), 44$s$ . . . third joint sensor (sensor), 42$a$, 43$a$, 44$a$ . . . actuator, 45 . . . gripper (holder), 50 . . . controller, 70 . . . surgical instrument, 72 . . . shaft, 73 . . . operating part, 90 . . . patient, 92 . . . body cavity, $P_p$ . . . pivot position (pivot point), L . . . axis (central axis)

MODE FOR CARRYING OUT THE INVENTION

Figure 1:
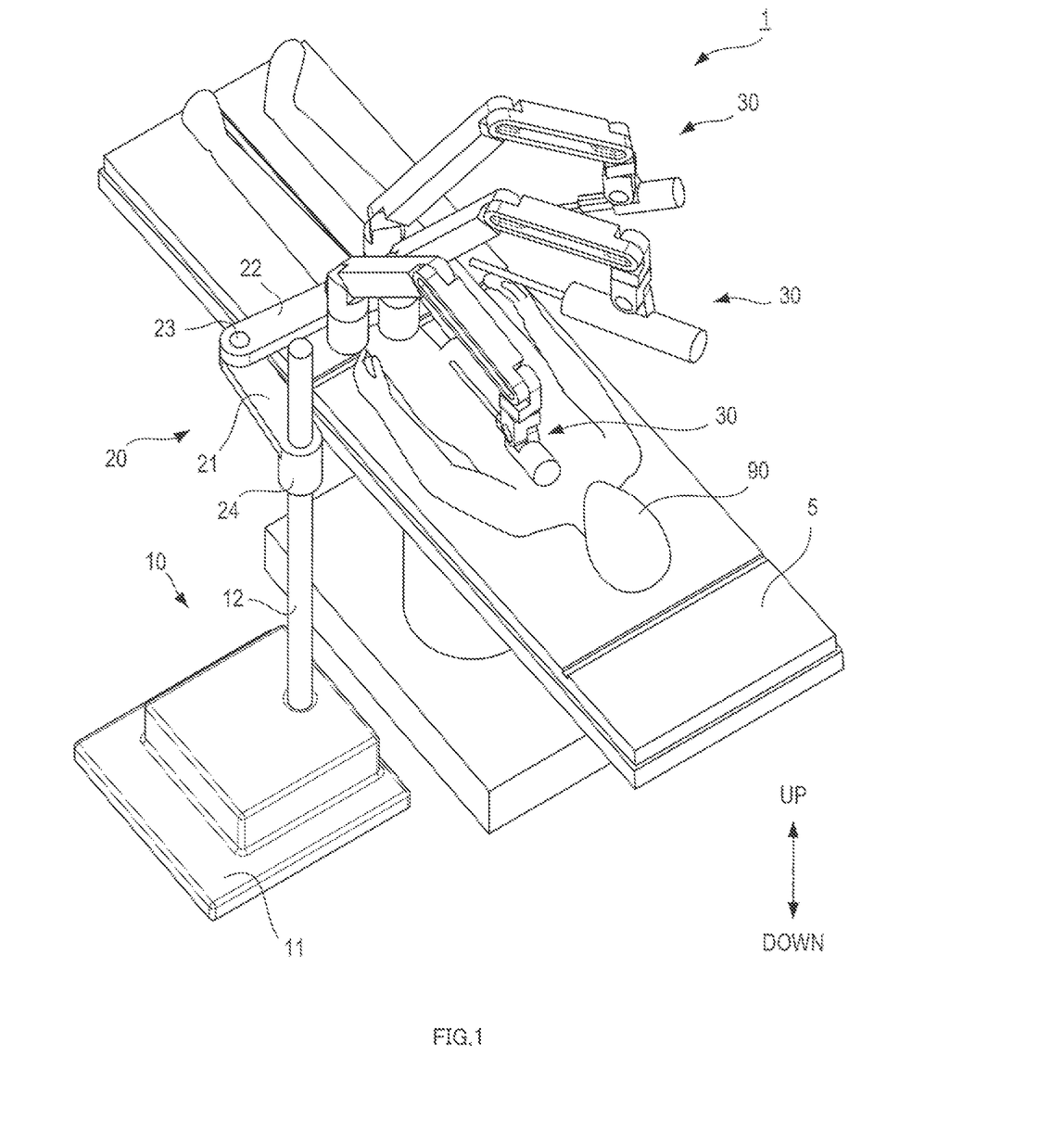
FIG. 1 is a perspective view explaining a configuration of a surgery assisting robot according to an embodiment of the present disclosure.
Figure 2:
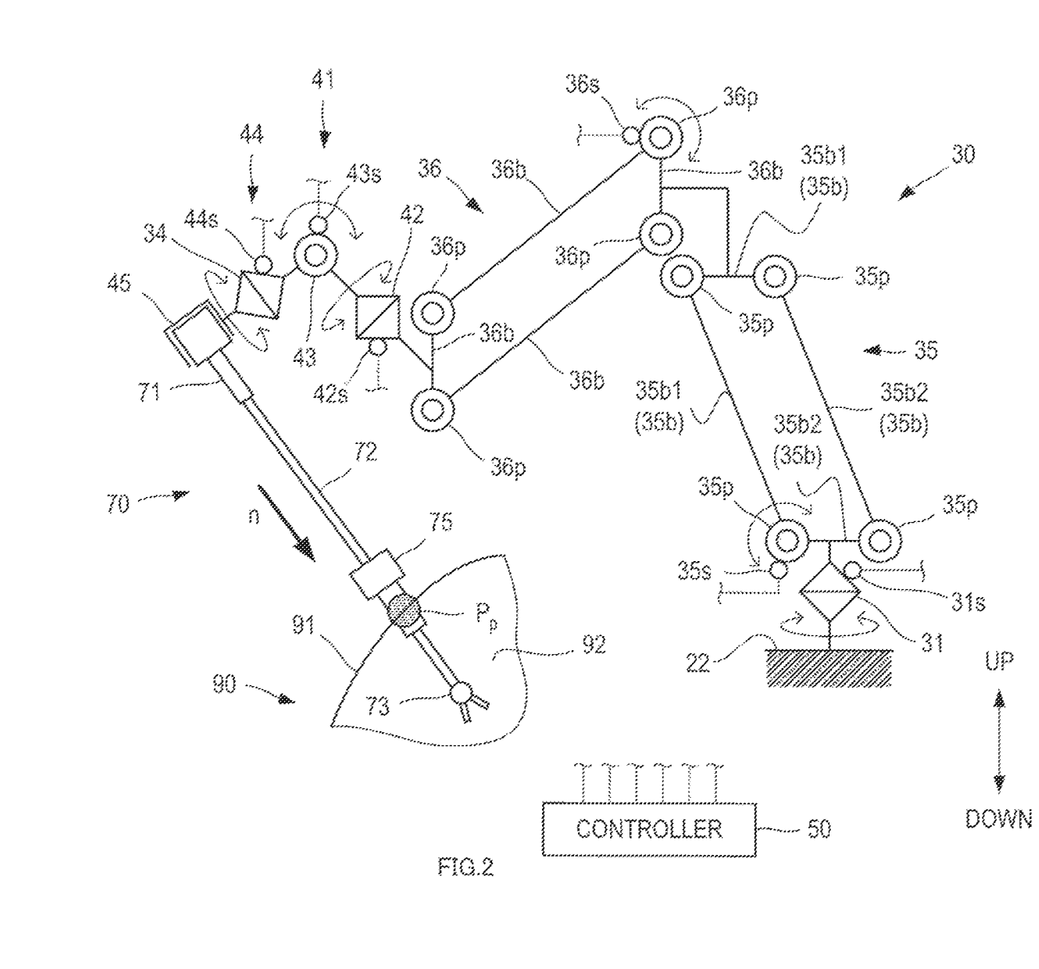
FIG. 2 is a schematic diagram explaining a configuration of a second arm in FIG. 1.

A surgery assisting robot (surgery assisting device) 1 according to an embodiment of the present disclosure will be described with reference to the drawings of FIGS. 1 to 8. The surgery assisting robot 1 of the present embodiment is a robot to assist endoscopic surgery. Specifically, as shown in FIGS. 1 and 2, the surgery assisting robot 1 is a robot capable of holding a surgical instrument 70 having an end to be inserted into a body cavity 92, which is a space inside an abdominal wall 91 of a patient 90. Also, the surgery assisting robot 1 is a robot capable of controlling at least one of a position or an orientation of the surgical instrument 70.

As shown in FIGS. 1 and 2, the surgery assisting robot 1 comprises a base 10, a first arm 20, second arms 30, and a controller 50. In the present embodiment, since the second arms 30 have the same configuration, the three second arms 30 will be described below without distinction. The present embodiment will be described as being applied to an example in which the number of the second arms 30 is three. The number of the second arms 30 may be larger or smaller than three.

The base 10 is configured to support the first arm 20 and the second arms 30. The present embodiment will be described as being applied to an example in which the base 10 is arranged in a position adjacent to a bed 5 on which the patient 90 lies. The base 10 comprises a bottom part 11 placed on a floor surface, and a pole 12 formed in a cylindrical shape extending upward from the bottom part 11.

The shape of the pole 12 is formed cylindrically as shown in FIG. 1. A peripheral surface, as a side part, of the cylindrically formed pole 12 is held by the first arm 20. This provides a configuration in which the first arm 20 can rotate about a cylindrical axial direction of the pole 12. Here, the axial direction of the pole 12 refers to a direction in which the pole 12 extends. The shape of the pole 12 is not limited to cylindrical. The shape of the pole 12 may be prismatic. In the case where the pole 12 is in a prismatic shape, the pole 12 may be provided with a structure to allow the first arm to rotate about the axial direction of the pole 12. The structure to allow the first arm 20 to rotate about the axial direction of the pole 12 does not have to be provided to the pole 12, and may be provided to the first arm 20.

The first arm 20 is arranged between the base 10 and the second arms 30. In other words, the first arm 20 is supported by the base 10, and the first arm 20 supports the second arms 30.

The first arm 20 comprises an arm portion 21 located closer to the base 10, an arm portion 22 located closer to the second arms 30, and a joint (first movable part) 23 located between the arm portion 21 and the arm portion 22.

The arm portion 21 is a member extending like a bar, and is provided, at its end (first end) closer to the base 10, with a fitting part (first movable part) 24 to be fitted to the pole 12 of the base 10. The fitting part 24 is configured to be capable of changing its arrangement position vertically along the pole 12, and also capable of changing an extending direction of the arm portion 21 about the pole 12, in other words, capable of rotating. That is, the fitting part 24 has a configuration achieving movement with two degrees of freedom. Examples of the configuration of the fitting part 24 to be used may include a configuration in which the pole 12 is inserted through a through-hole provided in the fitting part 24.

The arm portion 22 is a member extending like a bar, and at its end (second end) closer to the second arms 30, the second arms 30 are arranged. The arm portion 22 supports the second arms 30. The supported second arms 30 are supported so as to be rotatable about a vertically extending axis by the arm portion 22.

The joint 23 has a configuration provided between the arm portion 21 and the arm portion 22 and allowing the arm portion 21 and the arm portion 22 to be rotatable relative to each other about the vertically extending axis. That is, the joint 23 has a configuration achieving movement with one degree of freedom. Specific configuration of the joint 23 is not limited in particular.

Each second arm 30 supports the surgical instrument 70. The surgical instrument 70 is supported by the second arm 30 such that the position and the orientation of the surgical instrument 70 are changeable. Further, the second arm 30 is controlled such that the surgical instrument 70 passes through a pivot position $P_p$, which is a specified relative position with respect to the second arm 30, even when the position and/or the orientation of the surgical instrument 70 are/is changed. The pivot position $P_p$ substantially matches an arrangement position of a trocar 75 arranged in the abdominal wall 91 of the patient 90 who undergoes endoscopic surgical operation.

The position where the trocar 75 is arranged may be the abdominal wall 91 of the patient 90 as described above, or may be a chest wall. In the case where the trocar 75 is arranged, the pivot position $P_p$ is substantially matched to the arrangement position of the trocar 75. In the case where the trocar 75 is not arranged, the pivot position $P_p$ may be made to be substantially matched to a position of a through-hole or a port aperture provided in the abdominal wall 91.

The second arm 30 is arranged between the first arm 20 and the surgical instrument 70. In other words, the second arm 30 is supported by the first arm 20, and the second arm 30 is configured to be able to hold the surgical instrument 70.

As shown in FIG. 1, the second arm 30 is an arm that is arranged at a distal end (second end) of the first arm 20, which is an end on the side opposite to the base 10, and that is configured to be able to hold the surgical instrument 70.

The present embodiment will be described as being applied to an example in which only the second arms 30 are arranged at the distal end of the first arm 20. However, the configuration of the present disclosure is not limited to the configuration in which only the second arms 30 are arranged at the distal end of the first arm 20. For example, the second arms 30 and an arm device different from the second arms may be arranged in a mixed manner.

As shown in FIG. 2, the second arm 30 comprises a rotating part (second movable part) 31, a first link part 35, a second link part 36, a gimbal part 41, and a gripper (holder) 45. The rotating part 31, the first link part 35, and the second link part 36 are subjected to drive control based on control signals inputted from the controller 50 of the second arm 30.

Figure 3:
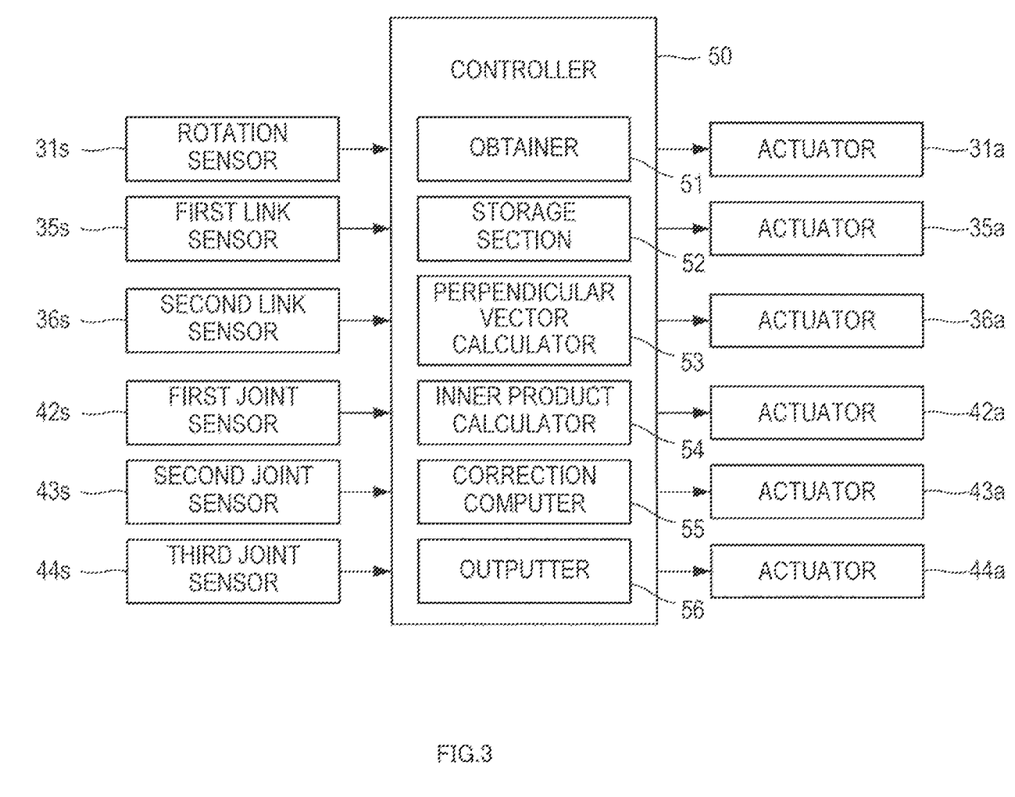
FIG. 3 is a block diagram explaining a configuration of a controller in FIG. 2.

The rotating part 31 is a joint arranged at a portion where the second arm 30 is secured to the first arm 20, and is driven by an actuator 31a shown in FIG. 3. The rotating part 31 is configured to be able to be driven to rotate about a rotation axis extending vertically. The rotating part 31 has a configuration achieving movement with one degree of freedom.

Specific configuration of the rotating part 31 is not limited to the configuration as described above. The rotating part 31 is provided with a rotation sensor (sensor) 31s to detect an angle of rotation of the rotating part 31.

The first link part 35 is arranged between the rotating part 31 and the second link part 36, and is driven by an actuator 35a shown in FIG. 3. The first link part 35 is formed like a rectangle. The first link part 35 is configured with two sets of bars 35b, and pins (second movable parts) 35p. Each of the two sets of bars 35b is configured with a pair of bars 35b1 and 35b2 arranged parallel to each other. The pins (second movable parts) 35p are positioned at respective ends of the bars 35b1 and the bars 35b2, which constitute the two sets of bars 35b. Corresponding ends of the bars 35b1 and 35b2 are connected to each other by the pin (second movable part) 35p. Each pin (second movable part) 35p allows rotation with one degree of freedom at a connected part, namely, at the corresponding end of the bars 35b1 and 35b2.

Further, the first link part 35 is provided with a first link sensor (sensor) 35s to detect an angle of rotation at a specified pin 35p. The present embodiment will be described as being applied to an example in which the first link part 35 is arranged in a vertically extending orientation.

The second link part 36 is arranged between the first link part 35 and the gimbal part 41, and is driven by an actuator 36a shown in FIG. 3. Similarly to the first link part 35, the second link part 36 is formed like a rectangle having two pairs of bars 36b arranged parallel to each other. The adjacent two bars 36b have a configuration connected by a pin (second movable part) 36p allowing rotation with one degree of freedom.

Further, the second link part 36 is provided with a second link sensor (sensor) 36s to detect an angle of rotation at a specified pin 36p. The present embodiment will be described as being applied to an example in which the second link part 36 is arranged in an orientation extending laterally (in a direction along a plane intersecting with a vertical direction).

The gimbal part 41 is arranged between the second link part 36 and the gripper 45. The gimbal part 41 comprises a first joint (second movable part) 42, a second joint (second movable part) 43, and a third joint (second movable part) 44, rotation axes of which intersect with one another, a first joint sensor (sensor) 42s to detect an angle of rotation of the first joint 42, a second joint sensor (sensor) 43s to detect an angle of rotation of the second joint 43, and a third joint sensor (sensor) 44s to detect an angle of rotation of the third joint 44.

The first joint 42, the second joint 43, and the third joint 44 are respectively driven by an actuator 42a, an actuator 43a, and an actuator 44a shown in FIG. 3.

The first joint 42 is arranged in a position adjacent to the second link part 36. The first joint 42 is arranged in an orientation in which its rotation axis extends diagonally upward With respect to a horizontal direction. The first joint 42 is more preferably arranged in an orientation extending diagonally upward at an angle of 45° with respect to the horizontal direction.

The second joint 43 is arranged between the first joint 42 and the third joint 44. The third joint 44 is arranged in a position adjacent to the gripper 45. The first joint 42, the second joint 43, and the third joint 44 each have a configuration to enable rotation about a rotation axis, namely, a configuration to allow for movement with one degree of freedom. The configurations of the first joint 42, the second joint 43, and the third joint 44 are not limited in particular.

The gripper 45 is arranged in a position adjacent to the gimbal part 41, in other words, at a distal end of the second arm 30. It suffices if the gripper 45 is configured to be able to grip the surgical instrument 70, and a configuration of the gripper 45 is not limited specifically.

The surgical instrument 70 is an instrument used in endoscopic surgical operation. As shown in FIG. 2, the surgical instrument 70 comprises a body part 71, a shaft 72 with a long shaft shape having an end to be inserted into a body cavity, and an operating part 73 arranged at the end of the shaft 72 and used for surgery operation.

The present embodiment will be described as being applied to an example in which the operating part 73 is forceps. The surgical instrument 70 may have forceps as in the present embodiment. Alternatively, the surgical instrument 70 may be other instruments used in endoscopic surgical operation, such as an endoscope, for example.

The body part 71 is a part gripped by the second arm 30, and contains a mechanism to transmit a driving force to drive the operating part 73 to the operating part 73. The mechanism to transmit the driving force to the operating part 73 is not limited in particular.

The shaft 72 is a member extending in a tubular shape or a rod shape, and is inserted through the trocar 75 to thereby be inserted inside the abdominal wall 91 of the patient. The shaft 72 contains a space used for transmission of the driving force from the body part 71 to the operating part 73.

The controller 50 estimates the pivot position $P_p$ in the surgical instrument 70 gripped by the second arm 30. Also, the controller 50 controls movement of the second arm 30. The pivot position P, in the surgical instrument 70 estimated by the controller 50 is used at least for control of the second arm 30. Here, the pivot position $P_p$ estimated by the controller 50 is represented by a coordinate system associated with the second arm 30.

The controller 50 is an information processing apparatus, such as a computer comprising a CPU (central processing unit), a ROM, a RAM, an input/output interface, and so on. A program stored in a storage device, such as the ROM described above, causes the CPU, the ROM, the RAM, and the input/output interface to work cooperatively to function as at least an obtainer 51, a storage section 52, a perpendicular vector calculator 53, an inner product calculator 54, a correction computer 55, and an outputter 56.

The obtainer 51 obtains information on the angles of rotation outputted from the rotation sensor 31s, the first link sensor 35s, the second link sensor 36s, the first joint sensor 42s, the second joint sensor 43s, and the third joint sensor 44s.

The obtainer 51 computes vector information, which is information on a vector n representing an orientation of the gripper 45 of the second arm 30 or the surgical instrument 70, based on the obtained information on the angles of rotation. Information on a first movement vector $\Delta P_p'$ representing movement of a provisional pivot position $P_p'$ to be described below, and information on a second movement vector $\Delta P_r$ representing movement of a rear end $P_r$, which is an end of the surgical instrument 70 closer to the gripper 45, is also computed similarly.

In the present embodiment, an explanation will be given of the case in which the second movement vector $\Delta P_r$ is a vector representing movement of the rear end $P_r$ in the surgical instrument 70; however, the second movement vector $\Delta P_r$ is not limited to the vector representing the movement at the rear end $P_r$. It suffices if the second movement vector $\Delta P_r$ is a vector representing movement at a position different from the provisional pivot position $P_p'$.

The storage section 52 stores a value of a provisional distance d' set in advance. The provisional distance d' is used for estimation of the pivot position $P_p$ relative to the second arm 30, together with a distal end position of the second arm 30 and the vector n representing the orientation of the surgical instrument 70.

Specifically, the provisional distance d' represents a distance from the distal end position of the second arm 30 to the provisional pivot position $P_p'$. The present embodiment will be described as being applied to an example in which the distal end position of the second arm 30 is a rear-end-side reference point of the surgical instrument 70 gripped by the second arm 30, for example, the rear end $P_r$ of the body part 71. That is, the length from the rear end $P_r$ of the surgical instrument 70 to the provisional pivot position $P_p'$ is the provisional distance d'.

Here, the provisional pivot position $P_p'$ is set in advance. The provisional pivot position $P_p'$ is used in estimating the true pivot position $P_p$. Thus, it does not matter whether the true pivot position $P_p$ and the provisional pivot position $P_p'$ match each other. It is preferred that the provisional pivot position $P_p'$ be set on the surgical instrument 70 to perform estimation.

The distal end position of the second arm 30 may be set to a front-end-side reference point, for example a front end, of the surgical instrument 70. In this case, as for the provisional distance d', the length from the front end of the surgical instrument 70 to the provisional pivot position $P_p'$ is the provisional distance d'.

The perpendicular vector calculator 53 calculates a direction of an axis L of the surgical instrument 70. Also, the perpendicular vector calculator 53 calculates a first perpendicular vector $\Delta P_p \perp'$ and a second perpendicular vector $\Delta P_r \perp$. Here, the direction of the axis L of the surgical instrument 70 is calculated based on the vector information. The first perpendicular vector $\Delta P_p \perp'$ and the second perpendicular vector $\Delta P_r \perp$ are perpendicular components relative to the direction of the axis L in the first movement vector $\Delta P_p'$ and the second movement vector $\Delta P_r$, respectively.

The inner product calculator 54 calculates a value of an inner product of the first perpendicular vector $\Delta P_p \perp'$ and the second perpendicular vector $\Delta P_r \perp$.

The correction computer 55 performs a computation of adding a value obtained by multiplying the value of the inner product by a specified coefficient k to the provisional distance d' stored in the storage section 52. Further, the correction computer 55 performs a processing for updating the stored value of the provisional distance d' to a new value of the provisional distance d' obtained by such computation.

The outputter 56 controls the movement of the second arm 30 by a single control system based on the information on the angles of rotation outputted from the rotation sensor 31s, the first link sensor 35s, the second link sensor 36s, the first joint sensor 42s, the second joint sensor 43s, and the third joint sensor 44s. In other words, the movement of the second arm 30 is controlled only by the outputter 56.

The outputter 56 outputs control signals for controlling at least one of a posture or an arrangement position of the second arm 30, also based on the estimated pivot position (pivot point) $P_p$. The present embodiment will be described as being applied to an example of outputting control signals for driving the actuator 31a, the actuator 35a, the actuator 36a, the actuator 42a, the actuator 43a, and the actuator 44a.

Specifically, the outputter 56 outputs control signals for controlling the pivot position $P_p$ set at any position on a long axis of the shaft 72 to be unchanged when at least one of the orientation or the arrangement position of the surgical instrument 70 is changed. Specific details of the arithmetic processing and details of the information processing for generating the control signals in the outputter 56 are not limited in particular.

The state in which a position of the pivot position $P_p$ is to be unchanged refers to a state in which a moving range of the pivot position $P_p$ falls within an acceptable range set in advance. Examples of the acceptable range may include a range within the trocar 75 (or the port aperture) arranged in the patient 90 and also including an intermediate position between an outer surface and an inner surface of the abdominal wall 91 or the chest wall of the patient 90, so that a load applied to tissue near a body surface of the patient 90 by the moving range of the pivot position $P_p$ falls within an extent to which the tissue is not damaged.

The present embodiment will be described as being applied to an example in which the controller 50 controls at least one of the posture or the arrangement position of the second arm 30. However, the posture of the second arm 30 may be controlled by a force applied from the outside. In other words, the controller 50 may change the posture of the second arm 30 actively. Alternatively, a configuration may be employed in which the posture of the second arm 30 is changed passively.

Here, examples of the force applied from the outside may include a force applied to the second arm 30 by contact between the trocar 75 and the surgical instrument 70, and a force applied by an operator who performs endoscopic surgery and/or an assistant who assists the operator in order to change the posture of the second arm 30.

Next, an explanation will be given of an arithmetic processing for estimating the pivot position $P_p$ by the controller 50 configured as described above. First, an equation that describes the pivot position $P_p$ will be explained with reference to FIG. 4. The pivot position $P_p$ is described by the following equation (1) using the rear end $P_r$ (distal end position of the second arm 30), the vector n, and a distance d.

Figure 4:
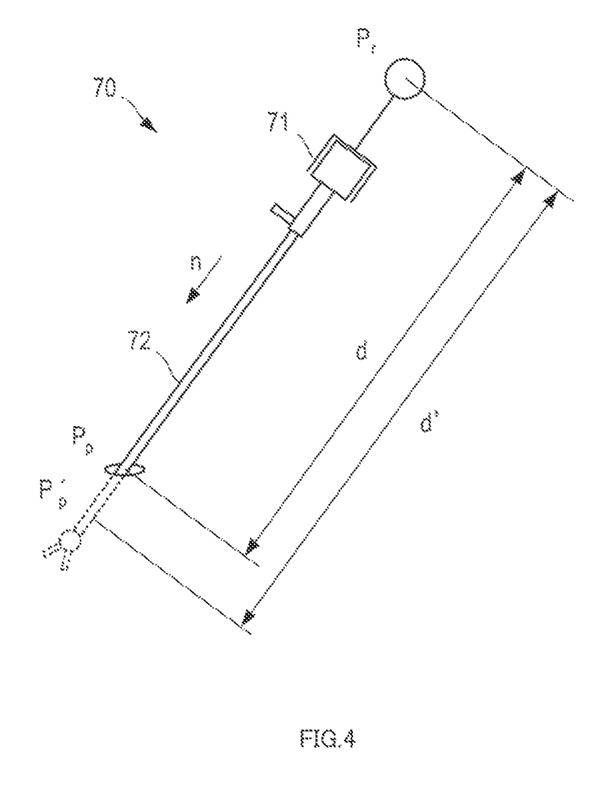
FIG. 4 is a diagram for explaining an equation that describes a pivot position.

[Equation 1]

$$P_p = P_r + dn \tag{1}$$

Next, the arithmetic processing for estimating the pivot position $P_p$ will be described. Upon start of the arithmetic processing for estimating the pivot position $P_p$ shown in FIG. 5, the controller 50 performs the arithmetic processing for estimation repeatedly in accordance with a sampling period set in advance. The arithmetic processing for estimation is continued at least until manipulation of the second arm 30 ends.

Figure 5:
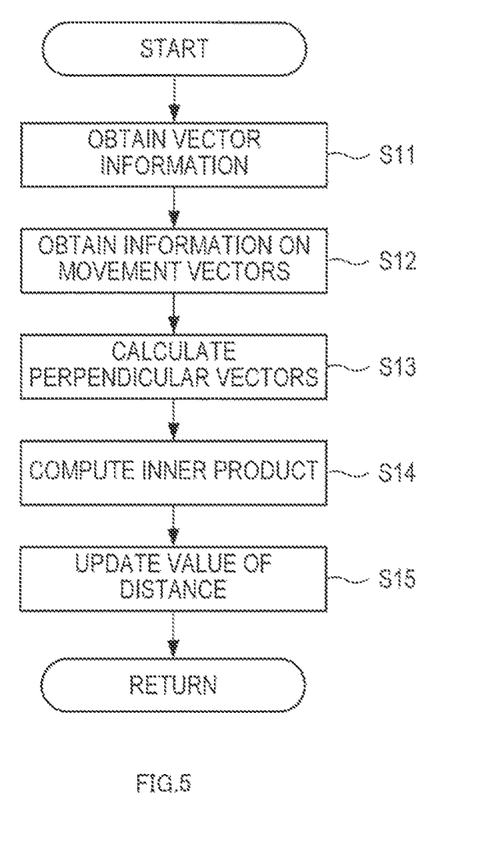
FIG. 5 is a flowchart explaining an arithmetic processing for estimating the pivot position.

First, the controller 50 performs, with the obtainer 51, a processing for obtaining the vector information, which is information on the vector n representing the orientation of the gripper 45 gripping the surgical instrument 70 in the second arm 30 or of the surgical instrument 70 (S11).

Specifically, the obtainer 51 performs a processing for obtaining the information on the angles of rotation outputted from the rotation sensor 31s, the first link sensor 35s, the second link sensor 36s, the first joint sensor 42s, the second joint sensor 43s, and the third joint sensor 44s (hereinafter also referred to as "the rotation sensor 31s and other sensors"). Then, the obtainer 51 performs an arithmetic processing for calculating the vector information, which is information on the vector n representing the orientation of the gripper 45 of the second arm 30 or of the surgical instrument 70, based on the obtained information on the angles of rotation.

Next, the obtainer 51 performs a processing for obtaining information on the first movement vector $\Delta P_p'$ and information on the second movement vector $\Delta P_r$ (S12). Specifically, the obtainer 51 performs an arithmetic processing for calculating the information on the first movement vector $\Delta P_p'$ and the information on the second movement vector $\Delta P_r$ based on the latest obtained information on the angles of rotation outputted from the rotation sensor 31s and other sensors and on the information on the angles of rotation obtained before that (e.g., during a further previous sampling period) and outputted from the rotation sensor 31s and other sensors.

After that, the controller 50 performs, with the perpendicular vector calculator 53, an arithmetic processing for calculating the first perpendicular vector $\Delta P_p \perp'$ and the second perpendicular vector $\Delta P_r \perp$ (S13). Specifically, the controller 50 first performs an arithmetic processing for calculating the direction of the axis L of the surgical instrument 70 based on the vector information as the information on the vector n.

Subsequently, the controller 50 performs an arithmetic processing for calculating each of the first perpendicular vector $\Delta P_p \perp'$ and the second perpendicular vector $\Delta P_r \perp$, which are perpendicular components with respect to the direction of the axis L of the surgical instrument 70, based on the information on the first movement vector $\Delta P_p'$, the information on the second movement vector $\Delta P_r$, and the direction of the axis L of the surgical instrument 70 (see FIG. 5).

Upon calculation of the first perpendicular vector $\Delta P_p \perp'$ and the second perpendicular vector $\Delta P_r \perp$, the controller 50 performs, with the inner product calculator 54, an arithmetic processing for calculating a value $\Delta d'$ of the inner product of the first perpendicular vector $\Delta P_p \perp'$ and the second perpendicular vector $\Delta P_p \perp$ (S14).

Figure 6:
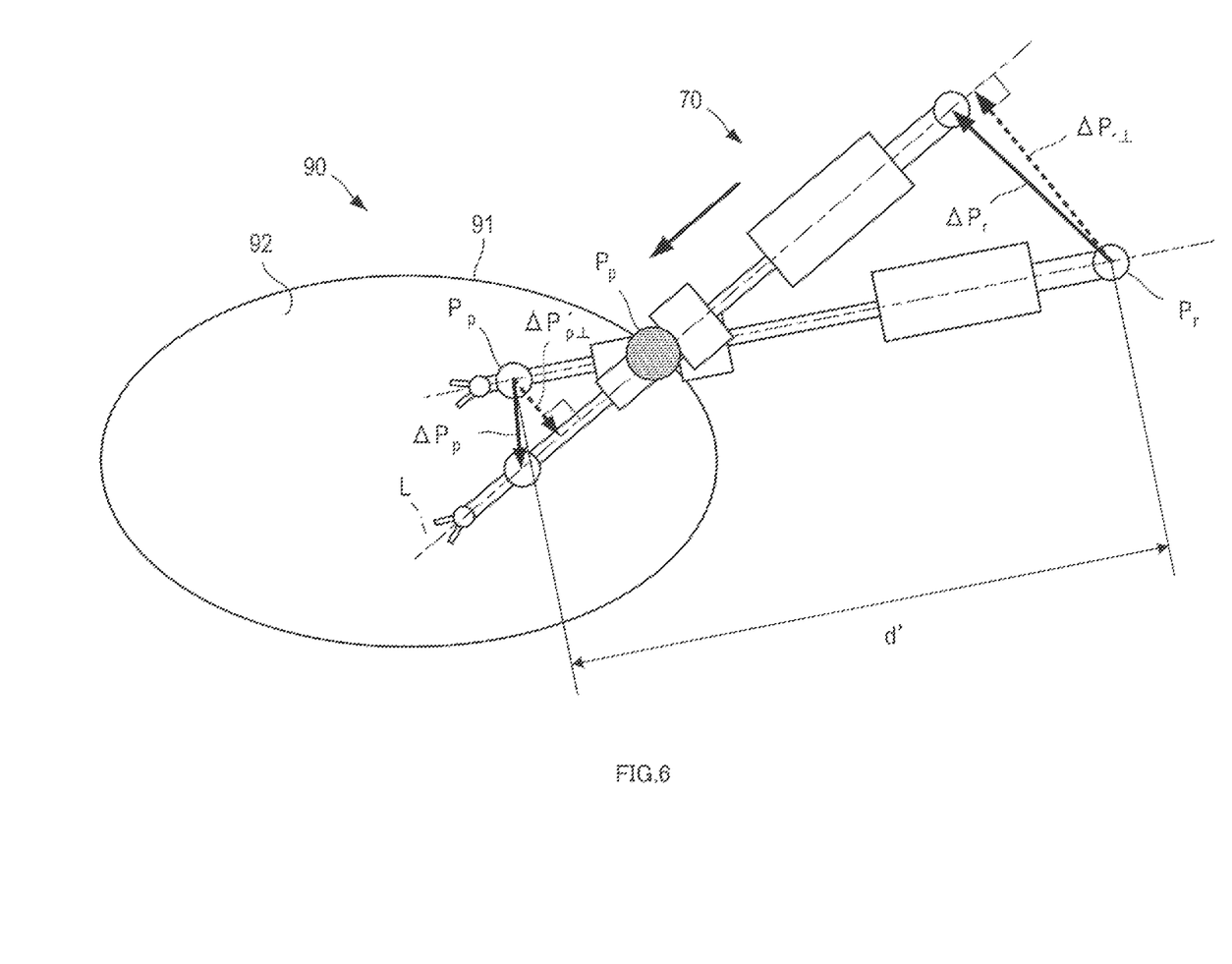
FIG. 6 is a schematic diagram explaining the arithmetic processing for estimating the pivot position.

For example, as shown in FIG. 6, in a case where the provisional distance d' is larger than the distance d being a true value, in other words, in a case where the provisional pivot position $P_p'$ is positioned more on a front end side of the surgical instrument 70 than the pivot position $P_p$, a direction of the first perpendicular vector $\Delta P_p \perp'$ and a direction of the second perpendicular vector $\Delta P_r \perp$ are opposite to each other. Therefore, the value $\Delta d'$ of the inner product of them is a negative value.

Figure 7:
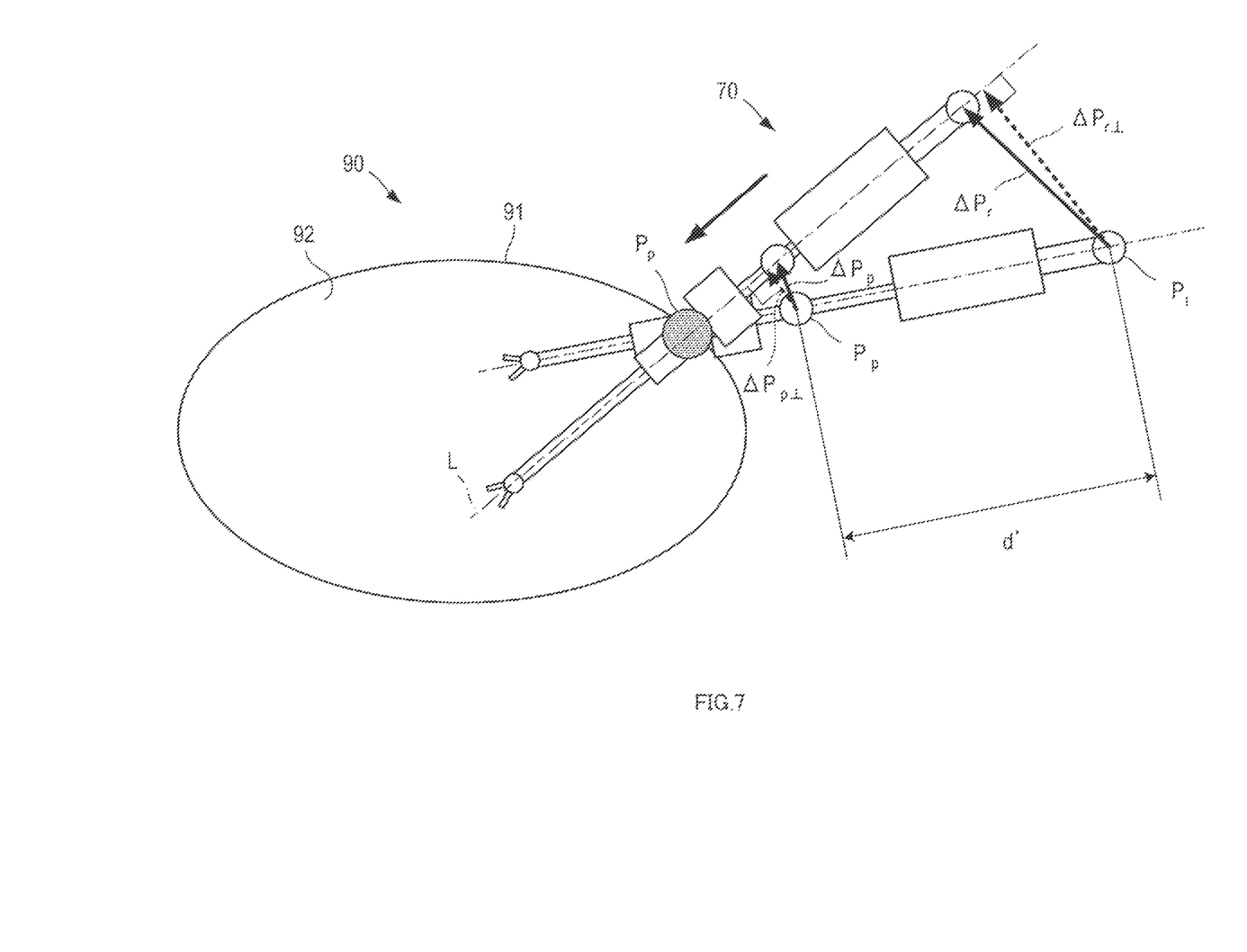
FIG. 7 is another schematic diagram explaining the arithmetic processing for estimating the pivot position.

On the other hand, as shown in FIG. 7, in a case where the provisional distance d' is smaller than the distance d being a true value, in other words, in a case where the provisional pivot position $P_p'$ is positioned closer to the rear end $\Delta P_r$ than the pivot position $P_p$, the direction of the first perpendicular vector $\Delta P_p \perp'$ and the direction of the second perpendicular vector $\Delta P_r \perp$ are the same as each other. Therefore, the value $\Delta d'$ of the inner product of them is a positive value.

Upon calculation of the value $\Delta d'$ of the inner product, the controller 50 performs, with the correction computer 55, an arithmetic processing for correcting and updating the provisional distance d' (S15). Specifically, the correction computer 55 performs a correction computation by adding a value obtained by multiplying the value $\Delta d'$ of the inner product by the specified coefficient k (where k is a positive value) to the provisional distance d' stored in the storage section 52. Further, the correction computer 55 performs a processing for updating the stored value of the provisional distance d' to a new value of the provisional distance d' obtained by such computation.

For example, in the case shown in FIG. 6, correction to decrease the provisional distance d' is performed, and correction to be closer to the distance d being a true value is performed. On the other hand, in the case shown in FIG. 7, correction to increase the provisional distance d' is performed, and correction to be closer to the distance d being a true value is performed.

The specified coefficient k may be set to a desired value. For example, when a value of the specified coefficient k is set larger, the provisional distance d' approaches the distance d being a true value sooner but may become less easy to converge to the distance d being a true value. In contrast, when the value is set smaller, the provisional distance d' approaches the distance d being a true value more slowly but becomes easy to converge to the distance d being a true value.

Figure 8:
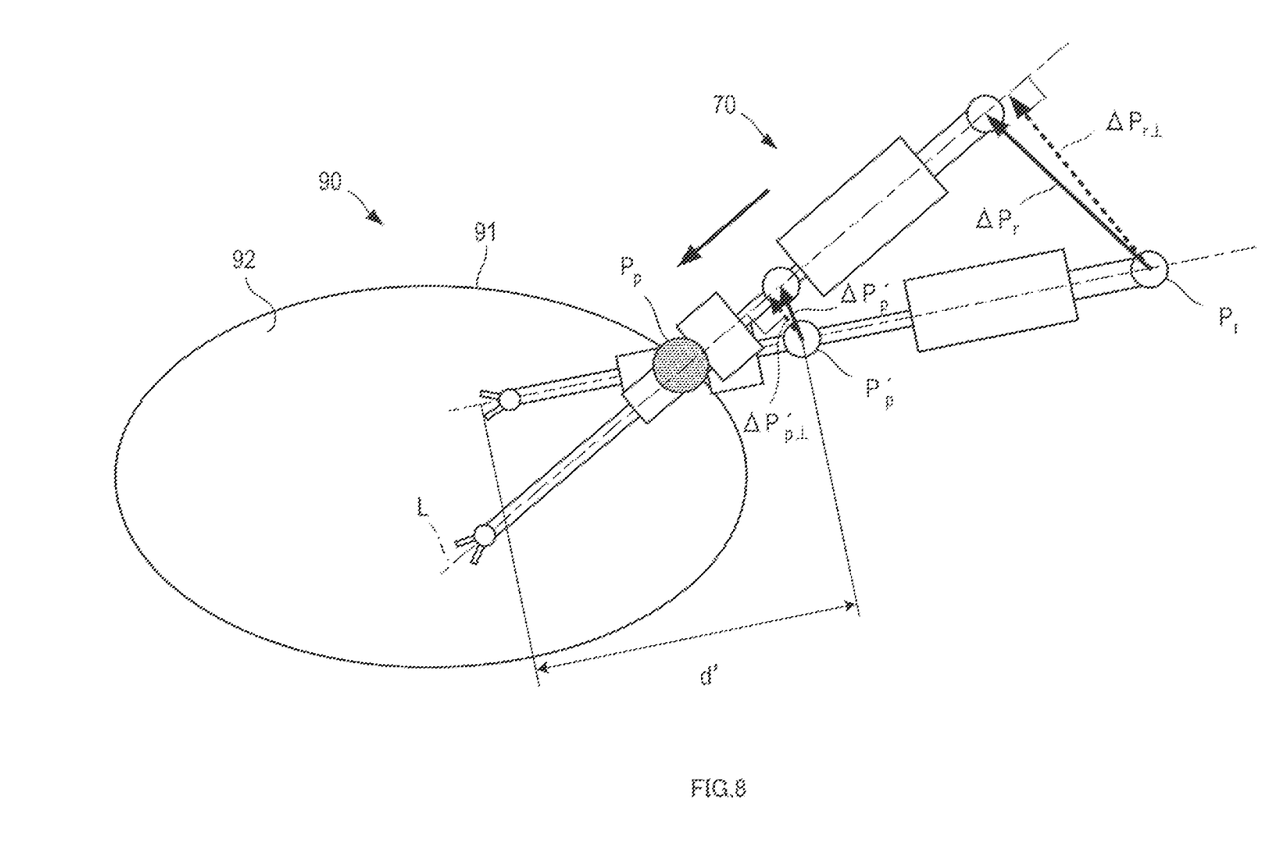
FIG. 8 is yet another schematic diagram explaining the arithmetic processing for estimating the pivot position.

In a case where the provisional distance d' represents a distance from the front end of the surgical instrument 70 to the provisional pivot position $P_p'$, increase/decrease in correcting the provisional distance d' in S15 becomes opposite, as shown in FIG. 8. Therefore, it is preferred that the specified coefficient k have a negative value.

The surgery assisting robot 1 configured as described above makes it possible to perform setting by manipulating only the second arm 30 due to provision of the second arm 30 with the rotating part 31, the pin 35p, the pin 36p, the first joint 42, the second joint 43, and the third joint 44, which achieve at least five degrees of freedom. For example, as compared with a case in which setting is performed by manipulating both set-up arms and manipulators like a technique described in Patent Document 1, the number of the manipulators to be manipulated is less, thus enabling easier setting.

Further, it is preferred that all of the rotating part 31, the pin 35p, the pin 36p, the first joint 42, the second joint 43, and the third joint 44 be configured to be operable in a state where the surgical instrument 70 is inserted in the body cavity. In other words, it is preferred that none of the rotating part 31, the pin 35p, the pin 36p, the first joint 42, the second joint 43, and the third joint 44 be fixed in movement, in the state where the surgical instrument 70 is inserted in the body cavity. "Fixed in movement" refers to a state where movement is unnecessary or not permitted during performance of surgery procedures.

Due to the configuration in which all of the rotating part 31, the pin 35p, the pin 36p, the first joint 42, the second joint 43, and the third joint 44 are operable in the state where the surgical instrument 70 is inserted in the body cavity, a movable range of the surgical instrument 70 is ensured more easily than in the technique described in Patent Document 1.

For example, the surgical instrument 70 inserted in the trocar 75 or the port aperture provided at the body surface of the patient 90 can be easily moved into another trocar 75 or port aperture. In addition, even when a relative position of the trocar 75 or the port aperture with respect to the surgery assisting robot 1 is changed for the reason such as increase/decrease in gas within the body cavity of the patient 90, the surgical instrument 70 is allowed to follow such change easily.

Due to the configuration in which the surgical instrument 70 can be held at the second end, being the distal end of the second arm 30, a movable range of the surgical instrument 70 is ensured more easily than in the technique described in Patent Document 1.

The surgical instrument 70 comprises the shaft 72 and the operating part 73. This makes it easier to insert the shaft 72 into the trocar 75 or the port aperture provided at the body surface of the patient 90 and to arrange the operating part 73 within the body cavity of the patient 90.

The controller 50 controls movements of the rotating part 31, the pin 35p, the pin 36p, the first joint 42, the second joint 43, and the third joint 44 so that the pivot position $P_p$ is located on the shaft 72. Thus, even when the orientation and/or the arrangement position of the surgical instrument 70 are/is changed, the shaft 72 can pass through the pivot position $P_p$. In other words, pivoting movement is enabled.

The pivoting movement in the second arm 30 is facilitated by estimating the location of the pivot position $P_p$ based on information on displacements in the rotating part 31, the pin 35p, the pin 36p, the first joint 42, the second joint 43, and the third joint 44. Further, control of the movements of the rotating part 31, the pin 35p, the pin 36p, the first joint 42, the second joint 43, and the third joint 44 by the controller 50 is enabled based on all of the information on the displacements in the rotating part 31, the pin 35p, the pin 36p, the first joint 42, the second joint 43, and the third joint 44. In other words, no case occurs in which, of the respective elements: the rotating part 31, the pin 35p, the pin 36p, the first joint 42, the second joint 43, and the third joint 44, some are controlled by the controller 50 and the others are controlled by a controller different from the controller 50. That is, the configuration is such that the movements of the rotating part 31, the pin 35p, the pin 36p, the first joint 42, the second joint 43, and the third joint 44 are controlled by a single control system, based on all of the information on the displacements in the rotating part 31, the pin 35p, the pin 36p, the first joint 42, the second joint 43, and the third joint 44.

The second arm 30 has three degrees of freedom, which are movements in three directions intersecting with one another in the surgical instrument 70, and two degrees of freedom, which are rotations about two axes intersecting with the axis L of the shaft 72 and also intersecting with each other. Thus, setting can be performed by manipulating only the second arm 30.

The technical scope of the present disclosure is not limited to the above-described embodiment. Various modifications may be made to the technical scope of the present disclosure within a range not departing from the spirit of the present disclosure. For example, although the example of the surgery assisting robot has been described in the above-described embodiment, the present disclosure is not limited to the form of a robot.

The invention claimed is:

1. A surgery assisting device configured to hold a surgical instrument having an end to be inserted into a body cavity of a patient, and configured to control at least one of a position or an orientation of the surgical instrument, the surgery assisting device comprising:
    a first arm that has a first end supported by a base and comprises a first movable part having movement with at least one degree of freedom; and
    second arms arranged at a second end of the first arm and configured to each hold the surgical instrument, the second arms each comprising second movable parts having movement with at least five degrees of freedom in total,
    wherein the second movable parts comprise a rotating part, a first link part, a second link part, and a gimbal part, the rotating part being arranged at a portion in which the second arm is secured to the first arm, the first link part being arranged between the rotating part and the second link part, and the second link part being arranged between the first link part and the gimbal part,
    wherein the rotating part is configured to rotate about a rotation axis extending in a vertical direction with one degree of freedom, and
    wherein each of the first link part and the second link part comprises a plurality of parallel links, each of the first link part and the second link part being configured to rotate about a rotation axis extending in a direction orthogonal to the vertical directions with a degree of freedom of rotation parallel to the other of the first link part or the second link part in the vertical direction.

2. The surgery assisting device according to claim 1, further comprising:
    a controller configured to control movements of the second movable parts with a single control system, based on information on displacements in the second movable parts.

3. The surgery assisting device according to claim 1, wherein a second end of each of the second arms is provided with a holder to hold the surgical instrument, the second end provided with the holder being on a side opposite to a first end supported by the first arm.

4. The surgery assisting device according to claim 1, wherein the surgical instrument comprises:
    a shaft with a long shaft shape having a first end to be inserted into the body cavity; and
    an operating part arranged at a second end opposite to the first end, having the shaft, inserted into the body cavity, and used for surgery operation.

5. The surgery assisting device according to claim 4, further comprising:
    a controller configured to control movements of the second movable parts,
    wherein the controller is configured to set a pivot point at a position on a long axis of the shaft, and to control the movements of the second movable parts so that the position of the pivot point is not changed when changing at least one of the orientation or an arrangement position of the surgical instrument.

6. The surgery assisting device according to claim 5, further comprising sensors configured to detect displacements in the second movable parts,
    wherein the controller is configured to perform an arithmetic processing for estimating the position of the pivot point based on information on the displacements detected by the sensors.

7. The surgery assisting device according to claim 4, wherein the second movable parts have three degrees of freedom corresponding to movements in three directions intersecting with one another in the surgical instrument, and two degrees of freedom corresponding to rotations about two axes intersecting with a central axis of the shaft and also intersecting with each other.

8. The surgery assisting device according to claim 2, wherein the surgical instrument comprises:
    a shaft with a long shaft shape having a first end to be inserted into the body cavity; and
    an operating part arranged at a second end opposite to the first end, having the shaft, inserted into the body cavity, and used for surgery operation.

9. The surgery assisting device according to claim 3, wherein the surgical instrument comprises:
    a shaft with a long shaft shape having a first end to be inserted into the body cavity; and
    an operating part arranged at a second end opposite to the first end, having the shaft, inserted into the body cavity, and used for surgery operation.

10. The surgery assisting device according to claim 5, wherein the second movable parts have three degrees of freedom corresponding to movements in three directions intersecting with one another in the surgical instrument, and two degrees of freedom corresponding to rotations about two axes intersecting with a central axis of the shaft and also intersecting with each other.

11. The surgery assisting device according to claim 6, wherein the second movable parts have three degrees of freedom corresponding to movements in three directions intersecting with one another in the surgical instrument, and two degrees of freedom corresponding to rotations about two axes intersecting with a central axis of the shaft and also intersecting with each other.

12. The surgery assisting device according to claim 1, wherein in a state in which the surgical instrument is inserted into the body cavity of a patient, the second movable parts are configured to be passively operable according to an external force applied through a trocar or a port aperture provided at a body surface of the patient.

13. The surgery assisting device according to claim 1, wherein the gimbal part has three degrees of freedom with rotational axes intersecting one another.

14. A surgery assisting device comprising:
a base;
a first arm that has a first end supported by the base, the first arm comprising a first movable part having at least one degree of freedom; and
a plurality of second arms arranged at a second end of the first arm, each of the plurality of second arms being configured to hold a surgical instrument, each of the plurality of second arms comprising a plurality of second movable parts, and each of the plurality of second arms having at least five degrees of freedom,
wherein the second movable parts comprises a rotating part, a first link part, a second link part, and a gimbal part, the rotating part being arranged at a portion in which the second arm is secured to the first arm, the first link part being arranged between the rotating part and the second link part, and the second link part being arranged between the first link part and the gimbal part,
wherein the rotating part is configured to rotate about a rotation axis extending in a vertical direction with one degree of freedom, and
wherein each of the first link part and the second link part comprises a plurality of parallel links, each of the first link part and the second link part being configured to rotate about a rotation axis extending in a direction orthogonal to the vertical directions with a degree of freedom of rotation parallel to the other of the first link part or the second link part in the vertical direction.

15. The surgery assisting device of claim 14, comprising:
a controller configured to control at least one of a position or an orientation of the surgical instrument.

16. The surgery assisting device of claim 15, wherein the controller is configured to control movements of the plurality of second movable parts based on information on displacements in the plurality of second movable parts.

17. The surgery assisting device of claim 15, wherein the controller drives the rotating part, the first link part, and the second link part to control the at least one of the position or the orientation of the surgical instrument.

18. The surgery assisting device according to claim 14, wherein each of the plurality of second arms includes a proximal end coupled to the first arm and a distal end provided with a gripper to hold the surgical instrument.

19. The surgery assisting device according to claim 18, wherein the surgical instrument comprises:
a shaft having a distal end to be inserted into a body cavity of a patient and a proximal end that is gripped by the gripper; and
an operating part arranged at the distal end of the shaft and used for surgery on the patient.

20. The surgery assisting device according to claim 14, wherein the surgical instrument comprises:
a shaft having a distal end to be inserted into a body cavity of a patient; and
an operating part arranged at the distal end and used for surgery on the patient.

21. The surgery assisting device according to claim 20, further comprising:
a controller configured to control movements of the plurality of second movable parts,
wherein the controller is configured to set a pivot point at a position on an axis of the shaft, and to control the movements of the plurality of second movable parts so that the pivot point is not changed when changing at least one of an orientation or an arrangement position of the surgical instrument.

* * * * *